(12) United States Patent
Swedberg et al.

(10) Patent No.: US 12,115,050 B2
(45) Date of Patent: Oct. 15, 2024

(54) MALE INCONTINENCE GUARD, KIT, AND METHOD

(71) Applicant: Essity Hygiene and Health Aktiebolag, Gothenburg (SE)

(72) Inventors: Maria Swedberg, Kungsbacka (SE); Anders Silfverstrand, Gothenburg (SE)

(73) Assignee: Essity Hygiene and Health Aktiebolag, Gothenburg (SE)

( * ) Notice: Subject to any disclaimer, the term of this patent is extended or adjusted under 35 U.S.C. 154(b) by 341 days.

(21) Appl. No.: 17/294,217

(22) PCT Filed: Dec. 13, 2018

(86) PCT No.: PCT/EP2018/084729
§ 371 (c)(1),
(2) Date: May 14, 2021

(87) PCT Pub. No.: WO2020/119902
PCT Pub. Date: Jun. 18, 2020

(65) Prior Publication Data
US 2021/0361494 A1 Nov. 25, 2021

(51) Int. Cl.
*A61F 13/471* (2006.01)
*A61F 13/15* (2006.01)
(Continued)

(52) U.S. Cl.
CPC ...... *A61F 13/471* (2013.01); *A61F 13/15731* (2013.01); *A61F 13/15747* (2013.01);
(Continued)

(58) Field of Classification Search
CPC .......... A61F 13/15731; A61F 13/15747; A61F 13/4704; A61F 13/471; A61F 13/551; A61F 13/5605; A61F 13/5611; A61F 13/625
See application file for complete search history.

(56) References Cited

U.S. PATENT DOCUMENTS 4,169,303 A   10/1979   Lemelson
4,290,174 A    9/1981   Kalleberg
(Continued)

FOREIGN PATENT DOCUMENTS

CN    1296401 A    5/2001
CN  101346118 A    1/2009
(Continued)

OTHER PUBLICATIONS

Office Action (Notification of the First Office Action) dated Oct. 27, 2021 by the China National Intellectual Property Administration (CNIPA) of the People's Republic of China in corresponding Chinese Patent Application No. 201880099992.4, and an English Translation of the Office Action. (18 pages).
(Continued)

*Primary Examiner* — Michele Kidwell
(74) *Attorney, Agent, or Firm* — Buchanan Ingersoll & Rooney PC

(57) ABSTRACT

A male incontinence guard including a fluid-impermeable backsheet, a fluid-permeable topsheet, and an absorbent body arranged between said backsheet and said topsheet is disclosed. The guard includes first and second fold lines along which side regions of the article can be folded to cover at least a portion of the absorbent surface of the article. Additional fold lines may be provided to facilitate folding of a lower end region over the first and second side regions. Fastening material is provided to secure the article in the folded configuration. Also, an associated method of manufacturing and a kit comprising an incontinence guard.

40 Claims, 8 Drawing Sheets

(51) Int. Cl.
*A61F 13/551* (2006.01)
*A61F 13/56* (2006.01)
*A61F 13/62* (2006.01)

(52) U.S. Cl.
CPC ........ *A61F 13/551* (2013.01); *A61F 13/5611* (2013.01); *A61F 13/625* (2013.01)

(56) References Cited

U.S. PATENT DOCUMENTS

| | | | |
|---|---|---|---|
| 5,037,417 | A | 8/1991 | Ternstrom |
| 5,413,568 | A | 5/1995 | Roach et al. |
| 5,531,732 | A | 7/1996 | Wood |
| 5,785,699 | A | 7/1998 | Schmitz |
| 6,001,527 | A | 12/1999 | Kawaguchi et al. |
| 6,036,679 | A | 3/2000 | Balzar et al. |
| 6,287,665 | B1 | 9/2001 | Hammer |
| 6,746,434 | B2 | 6/2004 | Johnson et al. |
| 7,018,496 | B1 | 3/2006 | George et al. |
| 7,744,576 | B2 * | 6/2010 | Busam ............. A61F 13/536 604/358 |
| 7,857,801 | B2 | 12/2010 | Hamall et al. |
| 8,197,458 | B2 | 6/2012 | Back |
| 8,298,205 | B2 | 10/2012 | Norrby et al. |
| 8,585,672 | B2 | 11/2013 | Lavon et al. |
| 8,663,184 | B2 | 3/2014 | Liu et al. |
| 8,784,722 | B2 | 7/2014 | Rocha |
| 8,979,815 | B2 * | 3/2015 | Roe ............. A61F 13/49406 604/385.01 |
| 9,216,118 | B2 * | 12/2015 | Roe ............. A61F 13/535 |
| 9,480,611 | B2 * | 11/2016 | Enz ............. A61F 13/15699 |
| 9,834,355 | B2 | 12/2017 | Dahlqvist et al. |
| 10,076,162 | B2 | 9/2018 | Rocha |
| 10,188,588 | B2 * | 1/2019 | Moszner ............. A61K 6/62 |
| 10,966,878 | B2 * | 4/2021 | Rudén ............. A61F 13/471 |
| 10,973,711 | B2 | 4/2021 | Swedberg et al. |
| 10,993,857 | B2 | 5/2021 | Swedberg et al. |
| 11,026,849 | B2 * | 6/2021 | Rudén ............. A61F 13/535 |
| 2002/0023321 | A1 | 2/2002 | Clune |
| 2003/0100878 | A1 | 5/2003 | Leak et al. |
| 2003/0120253 | A1 | 6/2003 | Wentzel et al. |
| 2006/0135022 | A1 | 6/2006 | Porter |
| 2008/0038507 | A1 | 2/2008 | Seth et al. |
| 2010/0180407 | A1 | 7/2010 | Rocha |
| 2010/0262111 | A1 | 10/2010 | Lindstrom |
| 2013/0030403 | A1 | 1/2013 | Bosaeus |
| 2013/0090618 | A1 | 4/2013 | Alshammari |
| 2016/0082688 | A1 | 3/2016 | Nakai et al. |
| 2017/0087034 | A1 | 3/2017 | Bosser |
| 2018/0104037 | A1 * | 4/2018 | Johnson ............. A61F 13/622 |
| 2019/0016058 | A1 | 1/2019 | Tuma |
| 2019/0254890 | A1 * | 8/2019 | Yonaha ............. A61F 13/476 |
| 2020/0214907 | A1 * | 7/2020 | Bremer ............. A61F 13/51496 |

FOREIGN PATENT DOCUMENTS

| | | |
|---|---|---|
| CN | 101500521 A | 8/2009 |
| CN | 101534778 A | 9/2009 |
| CN | 101641066 A | 2/2010 |
| CN | 101848691 A | 9/2010 |
| CN | 102341228 A | 2/2012 |
| CN | 102939062 A | 2/2013 |
| CN | 105517515 A | 4/2016 |
| CN | 106170276 A | 11/2016 |
| DE | 10102501 A1 | 8/2002 |
| DE | 10-2016-000756 A1 | 7/2017 |
| EP | 1529506 A1 | 5/2005 |
| EP | 2926787 A1 | 10/2015 |
| EP | 3047826 A1 | 7/2016 |
| EP | 3047827 A1 | 7/2016 |
| JP | H02501710 A | 6/1990 |
| JP | H10511868 A | 11/1998 |
| JP | 2000-000269 A | 1/2000 |
| JP | 2003-535649 A | 12/2003 |
| JP | 2011502569 A | 1/2011 |
| JP | 2014104147 A | 6/2014 |
| JP | 2015-058326 A | 3/2015 |
| JP | 2015058327 A | 3/2015 |
| RU | 2395265 C1 | 7/2010 |
| RU | 2396932 C2 | 8/2010 |
| RU | 2400199 C2 | 9/2010 |
| RU | 2404057 C2 | 11/2010 |
| TW | 201545729 A | 12/2015 |
| WO | 8804546 A1 | 6/1988 |
| WO | 95/30397 A1 | 11/1995 |
| WO | 96/20675 A1 | 7/1996 |
| WO | 99/53881 A1 | 10/1999 |
| WO | 00/27236 A1 | 5/2000 |
| WO | 0197738 A2 | 12/2001 |
| WO | 0226182 A2 | 12/2001 |
| WO | 2008060204 A1 | 5/2008 |
| WO | 2009061241 A1 | 5/2009 |
| WO | 2009/136826 A1 | 11/2009 |
| WO | 2010071517 A1 | 6/2010 |
| WO | 2010/085492 A1 | 7/2010 |
| WO | 2011/037502 A1 | 3/2011 |
| WO | 2011162657 A1 | 12/2011 |
| WO | 2011162658 A1 | 12/2011 |
| WO | 2012100823 A1 | 8/2012 |
| WO | 2013/162430 A1 | 10/2013 |
| WO | 2015/190964 A1 | 12/2015 |
| WO | 2015190966 A1 | 12/2015 |
| WO | 2016/081438 A1 | 5/2016 |
| WO | 2016/149243 A1 | 9/2016 |
| WO | 2018228682 A1 | 12/2018 |
| WO | 2018228710 A1 | 12/2018 |

OTHER PUBLICATIONS

International Search Report (PCT/ISA/210) and Written Opinion (PCT/ISA/237) dated Aug. 16, 2019, by the European Patent Office as the International Searching Authority for International Application No. PCT/EP2018/084729.
International Preliminary Report on Patentability (PCT/IPEA/409) dated Mar. 10, 2021, by the European Patent Office as the International Searching Authority for International Application No. PCT/EP2018/084729.
Written Opinion of the International Preliminary Examining Authority (PCT/IPEA/408) dated Nov. 4, 2020, by the European Patent Office as the International Searching Authority for International Application No. PCT/EP2018/084729.
Office Action (Notice of Reasons for Rejection) issued May 30, 2022, by the Japanese Patent Office in corresponding Japanese Patent Application No. 2021-533257 and an English Translation of the Office Action. (15 pages).
Office Action (Notification of the Second Office Action) issued Jul. 13, 2022, by the China National Intellectual Property Administration in corresponding Chinese Patent Application No. 201880099992.4 and an English Translation of the Office Action. (17 pages).
Office Action (Notification of the 3rd Office Action) issued Jan. 20, 2023, by the National Intellectual Property Administration, P. R. China in corresponding Chinese Patent Application No. 201880099992.4 and an English Translation of the Office Action. (16 pages).
Office Action issued on Dec. 5, 2022, by the Japanese Patent Office in corresponding Japanese Patent Application No. 2021-533257, and an English Translation of the Office Action. (5 pages).
Office Action (Decision of Rejection) issued on Mar. 31, 2023, by the Chinese Patent Office in corresponding Chinese Patent Application No. 201880099992.4, and an English Translation of the Office Action. (14 pages).

* cited by examiner

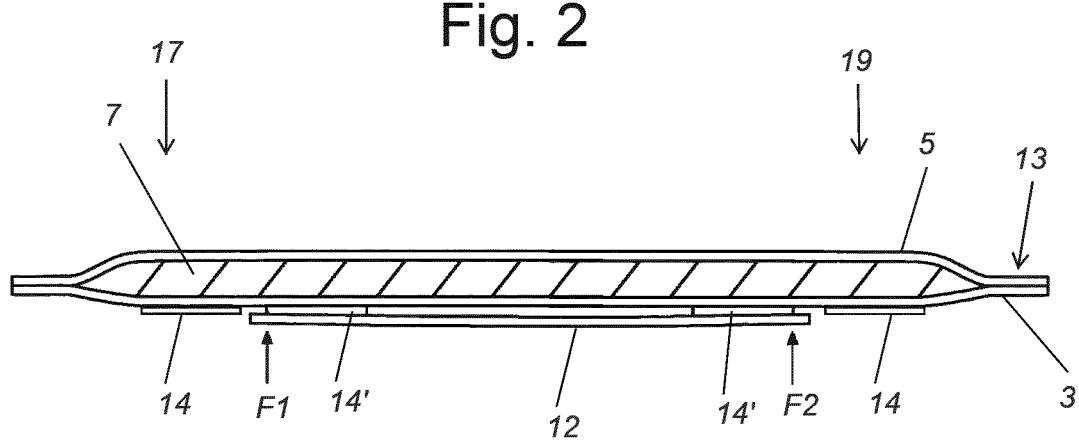
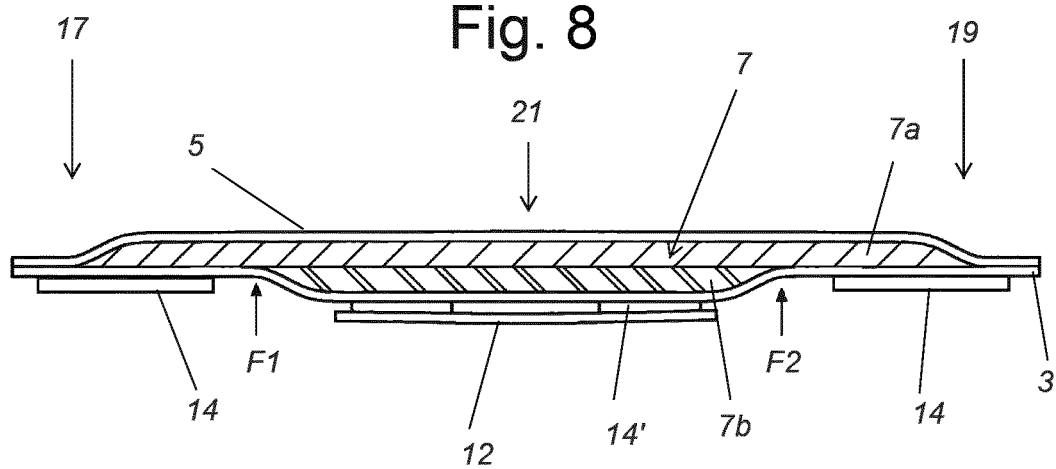

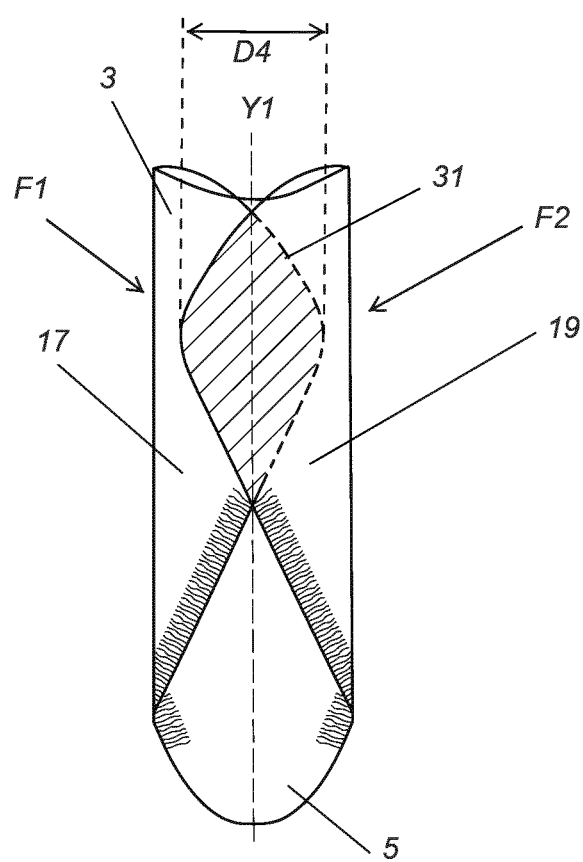

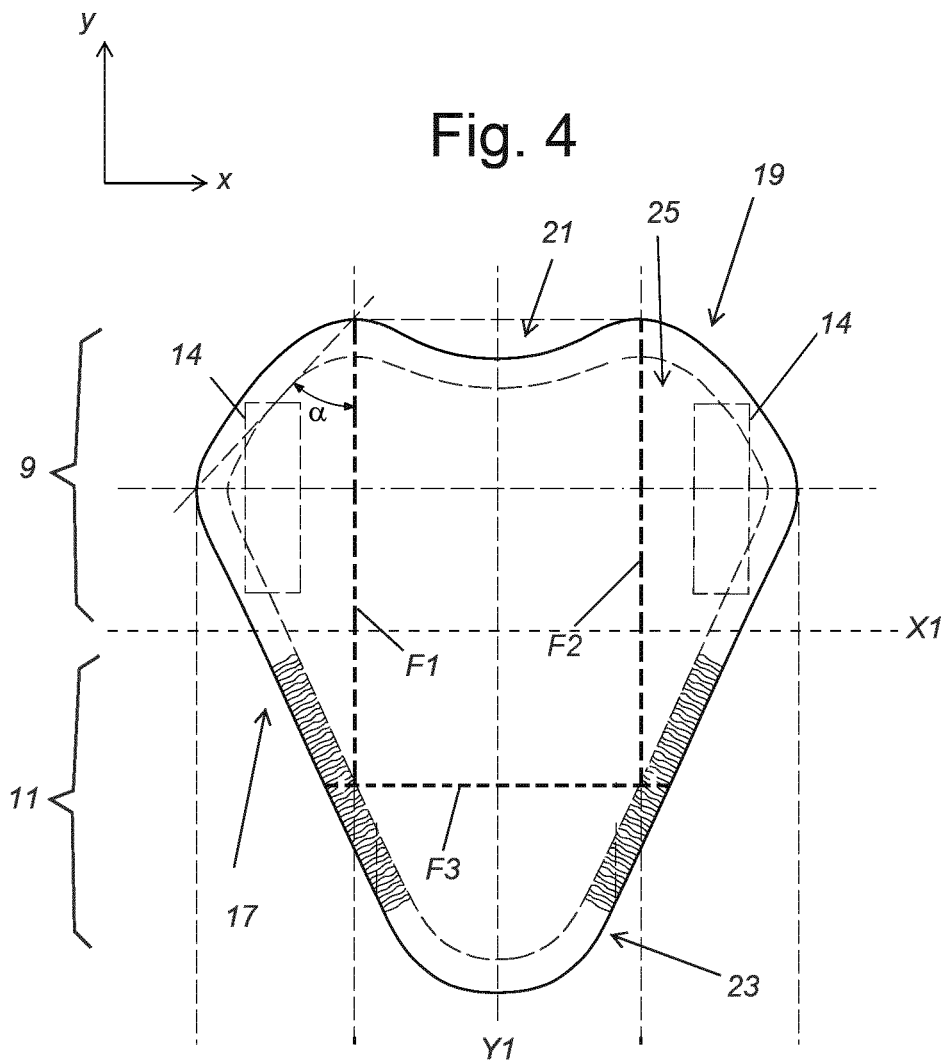

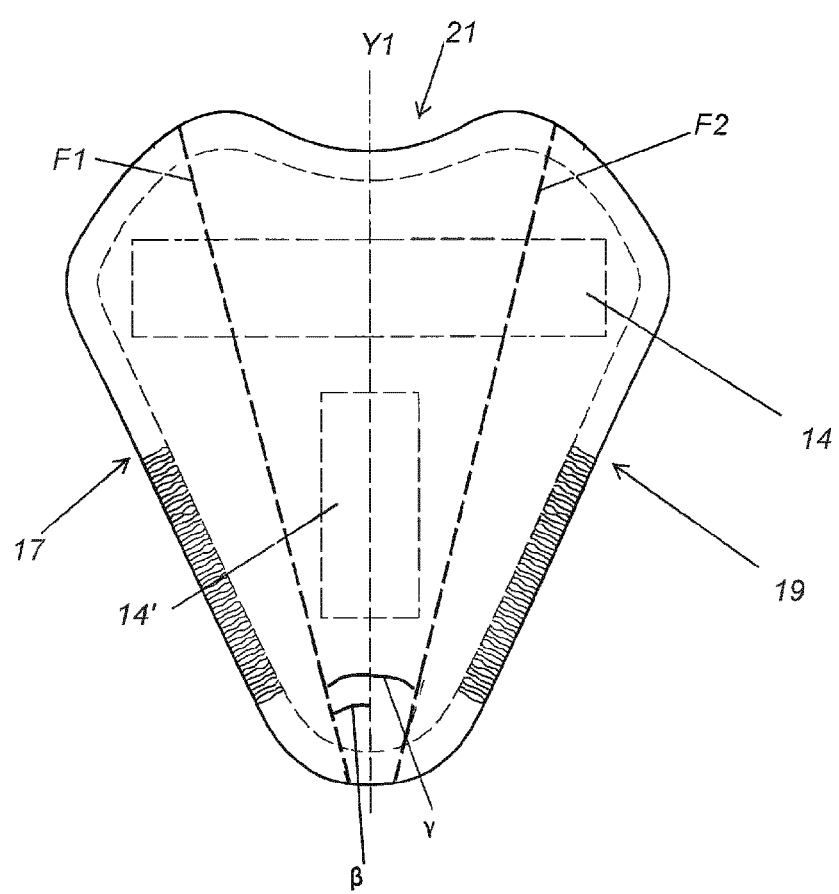

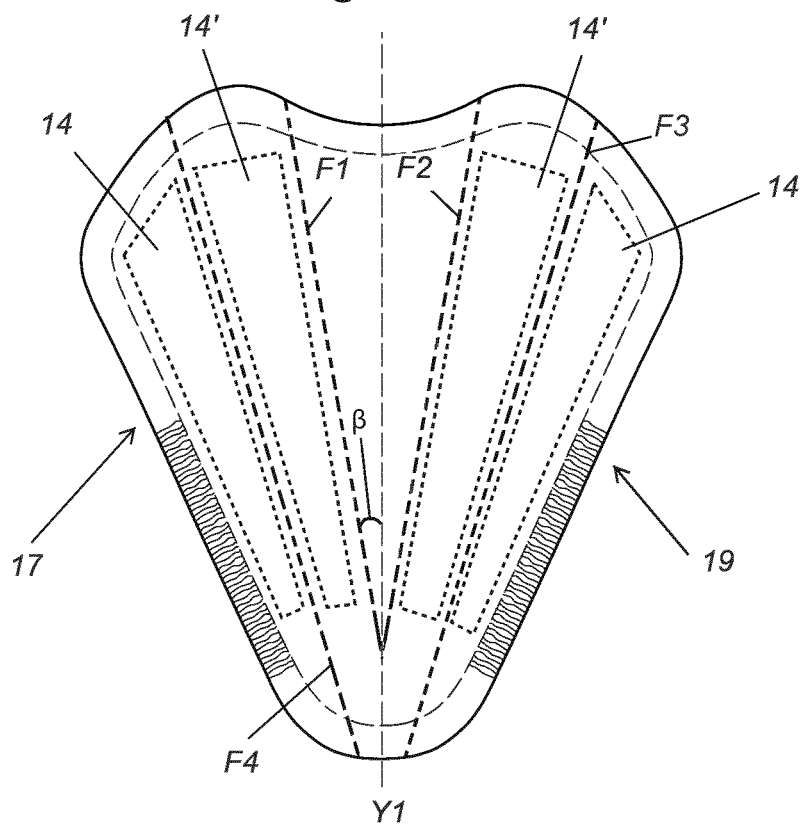

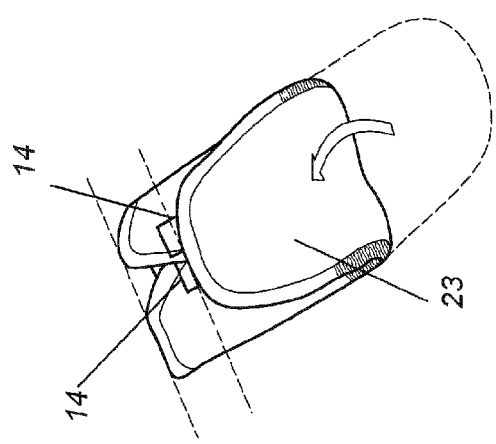
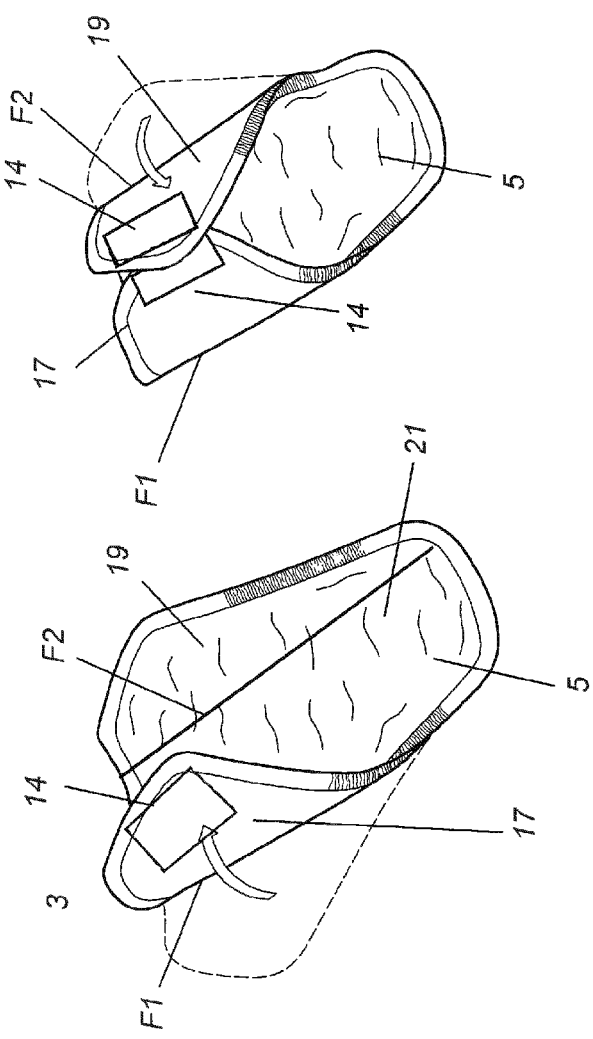

MALE INCONTINENCE GUARD, KIT, AND METHOD

TECHNICAL FIELD

The present disclosure relates to a male incontinence guard and a method for manufacturing such a male incontinence guard. The present disclosure further relates to a kit comprising a male incontinence guard.

BACKGROUND

Disposable absorbent articles, for example in the form of incontinence liners, baby diapers and sanitary napkins, are well known. The general purpose of such absorbent articles is to absorb, distribute, and store various types of body exudates, whilst providing a high level of comfort and sense of dryness to the wearer during use of the absorbent article. Such absorbent articles are also configured to protect the wearer's clothes from being soiled by such body exudates.

Absorbent articles in the form of incontinence articles are optimised to protect the wearer against urine leakage. Incontinence guards specifically configured for male wearers, are generally designed to cover the genital organs so as to protect against unwanted urine leakage. Many users, and in particular users who are otherwise not physically handicapped generally prefer not to use an incontinence guard in the form of diaper, since diapers may be considered to be bulky and indiscrete, and unsuitable for use with conventional clothing. Instead, special male incontinence guards, which are intended for men with light incontinence, have been developed so that they can maintain a normal lifestyle without inconvenience caused by incontinence. Such incontinence guards can be designed with an absorption capacity that is sufficient in order to absorb the fluid expected to be released into the absorbent article when it is worn.

Male incontinence guards are intended to be worn within the underwear to absorb urine leakage. Such guards are generally shaped to cover the male anatomy, and may be placed against an inner surface of the underwear, with or without fastening means. After use, the article is removed from the underwear, replaced with a new article (as required), and disposed of.

Light incontinence articles are generally designed with discretion for the user in mind. The colour, shape and size, and packaging of articles are thus varied to provide an article that provides the desired absorbency, provides a feeling of security, and can be discretely used by the wearer.

WO 2010/071517 describes a male incontinence guard comprising a body in which the front transverse edge is longer than the rear transverse edge. The male incontinence guard further has a central portion centred about a longitudinal centre line Y and at least a first side portion and a second side portion being arranged symmetrically on opposite sides of the central portion. The garment-facing surface of the guard comprises at least two adhesive zones located in said side portions and arranged so as to fix said guard to the garment of a user. The first and second side portions are folded over the body-facing surface of the central portion towards said longitudinal centre line Y. In the folded state, the adhesive zones are covered by a single strip of release material.

SUMMARY OF THE DISCLOSURE

It has been found that despite efforts to provide a comfortable, absorbent, and discrete male incontinence guard, there is still a need to improve the security and discretion of the article. In particular, there is a need to better secure the article in place within the underwear, and a need to provide an article that can be disposed of in a discrete manner, even where sanitary disposal facilities are not immediately available, which is common in male washroom facilities.

It is desired to provide a disposable hygiene article, such as a male incontinence guard, which can be conveniently and intuitively folded after use for disposal.

It is desired to provide a secure, comfortable, and form-fitting male incontinence guard which prevents leakage.

Yet another desire is to provide a pliable male incontinence guard which can be fastened to an undergarment and at the same time makes wearers feel comfortable and secure.

Yet another desire is to provide a male incontinence guard in which the guard remains securely in place within the undergarment without the corners becoming folded over during use.

Accordingly, in a first aspect of the invention, there is provided: a male incontinence guard comprising a fluid-impermeable backsheet, a fluid-permeable topsheet forming a body-facing surface of the guard, and an absorbent body arranged between said backsheet and said topsheet. The guard has a longitudinal extension along a longitudinal axis and a transverse extension along a transverse axis. The longitudinal axis divides the guard into left and right portions and the transverse axis divides the guard into an upper portion and a lower portion. The upper portion has a greater maximum extension in a transverse direction in a direction parallel to the transverse axis than the maximum extension of the lower portion in the transverse direction.

The guard is further divided into a first side region, a second side region, and a central region located between said first and side regions in a transverse direction. A first fold line is provided between the first side region and the central region and a second fold line is provided between the central region and the second side region. The first side region is configured to be folded over the central region along the first fold line and the second side region is configured to be folded over the central region along the second fold line, such that, when the first and second side regions are folded along the respective fold lines, the first side region at least partially overlaps the second side region to form a first overlap region.

The first and second fold lines are pre-formed or pre-determined fold lines. The fold lines may comprise a line along which the article is pre-folded, or they may comprise pre-determined lines along which folding is facilitated by means of the structure of the article.

At least one of the first and second side regions comprises a fastening material on a garment facing surface of the incontinence guard (e.g. the backsheet), with the fastening material being at least partially disposed in the first overlap region. The fastening material is configured to fasten to the topsheet of the guard and the topsheet and the fastening material are chosen accordingly.

As a result of the above configuration, the fastening material positioned on the garment facing surface of the article can be used to (i) fasten the article securely in place to the inside of an undergarment; and/or (ii) to fasten the first and second side regions together to cover an absorbent surface of the article after use.

The fastening material may be configured to fasten the first and second side regions to each other in a first folded configuration when the first and second side regions are folded along the first and second fold lines. The fastening material being at least partially disposed in the first overlap region is advantageous from the wearer's perspective since male incontinence guard is easier to fold and fasten after use. As a result of the easy folding and fastening, the male incontinence guard according to the present disclosure can meet a demand for articles that can be secured in a folded configuration before disposal at a later time, for example until the user has access to appropriate disposal facilities, which are often not present in male washroom environments.

A first distance $D_1$ can be defined between an outermost edge of the first side region and the first fold line and a second distance $D_2$ is defined between an outermost edge of the second region and the second fold line. A third distance $D_3$ can be defined between the first and second fold lines, wherein $D_1+D_2>D_3$. The distances $D_1$, $D_2$, and $D_3$ are measured in the transverse direction. Such a configuration can ensure that a region of overlap exists, in a transverse direction, between the first and second side regions of the article.

The first overlap region can be at least 10 mm in the transverse direction, more preferably at least 20 mm in the transverse direction, and more preferably at least 25 mm in the transverse direction.

The fastening material in the first overlap area can have an area covering at least 30% of the area of the first overlap region, more preferably at least 50% of the first overlap region, and more preferably at least 70% of the first region area. To this end, the fastening material can be configured as a continuous area of fastening material, patterned region of fastening material, or a plurality of discrete islands of fastening material.

Advantageously, in the first folded configuration, the first and second side regions can substantially completely cover an absorbing surface of the guard in the upper portion of the guard. The absorbent surface of the guard can for example be the topsheet and any underlying material such as an absorbent body (core) and/or an optional, additional liquid acquisition layer. This arrangement can ensure that the wetted portion of the article is covered when the article is in the folded configuration.

Although the above described advantages can be provided with fastening material provided on only one of the first and second side regions, it is preferred that the first and second side regions both comprise fastening material on the garment facing surface. By providing fastening material on both sides, the article can be held securely within the underwear on both sides, and the side regions can be secured together when folded along the fold lines, irrespective of whether the first or second side region is folded over first.

In at least some embodiments, the first and second fold lines are parallel to each other. The first and second fold lines can extend in a longitudinal direction, parallel to the longitudinal axis. In alternative embodiments, the first and second fold lines can diverge from each other as they extend in an upward direction (from a lower edge of the article toward an upper edge).

The first and second fold lines can be arranged symmetrically about the longitudinal axis. Symmetrical arrangement of the fold lines can provide improve the manner in which the article conforms to the user's anatomy during use, and the intuitiveness with which the article can be folded and secured for disposal after use.

The article, i.e. the incontinence guard, can comprise a third fold line, preferably extending in the transverse direction, to define a lower end region below the third fold line. The third fold line can provide an additional region to be folded over the first and second side regions, which results in a closed, folded package, with no portion of the absorbent surface exposed, which can thus be conveniently disposed of.

The third fold line can be configured such that, when the article is in first folded configuration (with the first and second side regions folded along the first and second fold lines), the lower end region can be folded along the third fold line to form a second folded configuration in which the lower end at least partially overlaps the first and second side regions in a second region of overlap. The second region of overlap allow the lower end region to be secured to the first and/or second side regions to maintain the article in the second folded configuration. To this end, fastening material on the first and second side regions is preferably provided such that it extends at least partially in the second overlap region. The fastening material in the second overlap region can be the same fastening material that extends in the first and second side regions, however, additional fastening material may also be provided.

Advantageously, when the guard is in the second folded configuration (with both side regions and the lower end region folded along the first, second and third fold lines), the absorbent surface of the guard is substantially completely covered.

The first and second overlap regions may at least partially overlap each other. However, it will be appreciated that a region of overlap may be provided between the lower end region and at least one of the first and second side panels in a region that falls outside of the first overlap region.

The third fold line can extend in a transverse direction in the lower portion of the guard, e.g. below the transverse axis. However, it will be appreciated that the third fold line may extend along the transverse axis, or above the transverse axis. The third fold line can extend parallel with the transverse axis or in an angle.

The third fold line can be perpendicular to the first and second fold lines and/or it can intersect one or both of the first and second fold lines. The fold lines can be straight or curved, the precise configuration can be chosen based on the size, shape, and configuration of the incontinence guard.

The fold lines can take many forms. The fold lines may be provided by pre-folding the article, or by a structural feature configured to provide a region of increased pliability along which the article can fold. As mentioned above, the fold lines provide a predetermined line along which the article can be folded after use. The fold line can therefore be provided by the core or by the backsheet, fastening material, or additional layers in the article. Fold lines formed in the core can comprise, for example, compression lines, embossed regions, score lines, channels in the core having a lower basis weight, etc. Alternatively, fold lines may be formed, for example, by an edge of a fastening material region, a space between two regions of fastening material (in which no fastening material is present), or by the edge of an additional layer incorporated into the article, such as an additional absorbent layer, a film or a reinforcing layer. Weld lines (e.g. ultrasonic weld lines) may also provide fold lines suitable for use in the context of the present disclosure.

The fold lines can be continuous or discontinuous. By discontinuous it is meant that the fold line can comprise a plurality of discrete fold line sections, e.g. a dashed compression or embossing line.

The fastening material is configured to engage the topsheet of the guard to secure the guard in a folded configuration. The fastening material and the topsheet material can thus be chosen to ensure that the fastening material fastens to the topsheet material. The fastening material should engage the topsheet material such that the guard can be held in the folded configuration, in particular after use.

The fastening material can be a mechanical fastening material, such as a hook patch. Hook regions may also be integrally provided on the backsheet. To provide an engagement surface for the mechanical fastening on the backsheet, the topsheet can comprise a material configured to engage a hook fastening, such as a woven material, a non-woven material, a spunbond material, a carded material, a spun lace material, or a combination of the above.

The fastening material can also comprise an adhesive and the topsheet can be formed of a material configured to engage the adhesive to secure the guard in the folded configuration. Suitable materials include polyolefinic apertured film, a laminate or a combination thereof. Adhesive fastenings may also be combined with mechanical fastenings.

The backsheet may comprise a single liquid-impermeable layer or it can comprise multiple layers, e.g. a multi-layer. The backsheet is facing away from the user during use, and is opposite to the body facing topsheet layer of the absorbent article. The backsheet may be a liquid-impermeable or fluid repellant structure. The backsheet material may be of a breathable or non-breathable material such as a of a film, a nonwoven or a laminate thereof, or a foam. The backsheet may have a laminate structure comprising a liquid barrier film and a nonwoven layer arranged on top of each other, wherein the nonwoven layer is arranged at an outer side away from the wearer of the absorbent article when worn. The backsheet may be elastic in any direction.

The film may be of a thermoplastic polymer, e.g. a polyester such as PET or of polyolefins such as of polyethylene or polypropylene, or a mixture thereof. It may be a single layer film or a multi layer film.

The nonwoven may be of thermoplastic polymer material fibers or filaments e.g. a polyester such as PET or of polyolefins such as of polyethylene or polypropylene, or a mixture thereof. The nonwoven may be formed by a variety of different processes, such as spunbonding, airlaying, meltblowing or bonded carded web formation processes. The nonwoven layer may be made of an SMS (spunbond/meltblown/spunbond) or SS (spunbond/spunbond) nonwoven material of polypropylene or bicomponent fibers of polypropylene and polyethylene, or of a combination of such materials.

Forming the liquid barrier film of a plastic material, such as a thermoplastic film material, allows for a particularly good printability of the liquid barrier sheet.

The liquid barrier film may consist of a single layer or have a laminate structure with a plurality of layers, e.g., two or more layers, three or more layers, or four or more layers. The layers of the laminate structure may be laminated, bonded or attached to each other, for example, by thermo and/or mechanical bonding, such as thermo-sealing, ultrasonic bonding, such as ultrasonic welding, an adhesive or adhesives, stitching or the like.

The liquid barrier film may be a breathable microporous film. The microporous film may be made of a material comprising at least two basic components, namely a thermoplastic elastomeric polyolefin polymer and a filler. These components and, in some embodiments, additional other components may be mixed together, heated and subsequently extruded into a mono-layer or multi-layer film using any one of various film-producing processes, such as cast embossed, chill and flat cast, and blown film processes.

Where the backsheet comprises multiple layers or a multi-layer laminate, the outermost layer (that provides the garment facing surface in use) comprises the fastening material.

The topsheet can also comprise a single layer or multiple layers, e.g. a multi-layer laminate. Where the topsheet comprises multiple layers or a multi-layer laminate, the outermost layer (that provides the body facing surface during use) comprises the material configured to engage the fastening material.

The topsheet is a fluid pervious body facing structure that may be sufficiently liquid-permeable to allow discharged body fluids to penetrate through its thickness. The topsheet may be suitably manufactured from a material which is compliant and soft-feeling to the skin of the wearer. The topsheet may consist of a single layer or have a laminate structure comprising a plurality of layers, for example, two or more layers. The layers may be made of the same material, or some or all the layers may be made of different materials. The topsheet material may be of a nonwoven, a film or a laminate thereof or of a foam. The material may be of thermoplastic synthetic or natural fibers, or a mixture thereof. Natural fibers may be e.g. cotton or pulp fibers and synthetic fibers may be e.g. of a polyester such as PET or a polyolefin such as polyethylene or polypropylene, or a combination of these fibers. The nonwoven may be formed by a variety of different processes, such as spunbonding, airlaying, meltblowing or bonded carded web formation processes. The nonwoven layer may be made of an SMS (spunbond/meltblown/spunbond) or SS (spunbond/spunbond) nonwoven material of polypropylene or bicomponent fibers of polypropylene and polyethylene, or of a combination of such materials.

The topsheet layer or layers may be apertured or non-apertured and may have imparted hydrophilic properties to improve liquid drainage of the structure. The topsheet may have a basis weight in the range of 5-40 g/m2.

The absorbent core, i.e. body provided between the topsheet and the backsheet to absorb the liquid, such as urine or other bodily fluids, which has passed through the topsheet. The absorbent core may be made of one layer only, made from any suitable absorbent or liquid uptake material, such as one or more layers of cellulose fluff pulp, foam, fiber waddings or the like.

The absorbent core may comprise suitable amounts of superabsorbent particles. Such superabsorbent material is well known in the field of absorbent articles, and is constituted by a water-swellable and water-insoluble material which is capable of absorbing large quantities of fluid upon formation of a hydrogel. The absorbent core may contain superabsorbent material in the form of fibers or particles of absorbent polymer material. For example, the superabsorbent material may be surface cross-linked, partially neutralized polyacrylates. Furthermore, a core cover may surround the core and may be made of nonwoven material, with a basis weight of 5-20 g/m2.

The superabsorbent material, e.g., the superabsorbent fibers or particles, may be mixed with other absorbent or liquid uptake material or materials, such as cellulose fluff pulp, and/or arranged in pockets or layers in the absorbent core.

The absorbent core may further comprise components for improving the properties of the absorbent core. For example, the absorbent core may comprise a binder or binders, such as binder fibers.

An acquisition and distribution layer (ADL) may be arranged between the absorbent core and the topsheet. The acquisition layer may be adapted to quickly receive and temporarily store discharged liquid before it is absorbed by the absorbent core Furthermore, as known by the skilled person, the various layers of the absorbent article may be attached by means of adhesive material.

Additional fastening material may be provided outside the first overlap region, for example in the first and second regions of the guard or in the central region of the guard, to provide a fastening surface for fastening the guard within the underwear of the user. The additional fastening material can also be an adhesive or mechanical fastening material, such as a hook patch or hook regions integrally provided in the backsheet.

Advantageously, the first and second fold lines are substantially free of fastening material. Leaving the first and second fold lines (and optionally the third fold line) free of fastening material may facilitate fold of the article along the predetermined fold lines.

In a second aspect of the invention, there is provided a method for manufacturing a male incontinence guard. The method comprises the steps of: providing a fluid-impermeable backsheet, a fluid-permeable topsheet, and an absorbent body arranged between the backsheet and the topsheet; forming a first fold line and a second fold line in said guard, wherein the first and second fold lines divide the guard into a first side region, a second side region and a central region, with the first fold line being defined between the first side region and the central region and the second fold line being defined between the central region and the second side region. The first side region is configured to be folded along the first fold line over the central region and the second side region is configured to be folded along the second fold line over the central region such that the first side region at least partially overlaps the second side region to form a first overlap region. According to the method, a fastening material is provided on the backsheet in at least one of the first and second regions, disposed at least partially in the first overlap region.

The method may further comprise the step of forming a third fold line to define a lower end region below the third fold Line. The third fold line is configured to provide a predetermined line along which the lower end region can be folded to overlap with at least one of the first and second side regions.

One or more of the first, second, and third fold lines may be formed by embossing or compressing the absorbent core of the article, or by providing a channel in the core comprising a lower basis weight than adjacent regions of the core.

One or more of the first, second, and third fold lines may be formed by an additional layer in the central region of the guard, with the fold lines formed by an edge of the additional layer. The additional layer may comprise an additional absorbent layer, a film, or a reinforcing layer.

One or more of the first, second, and third fold lines may be formed by an edge of the fastening material, or a space in which no fastening material is present.

The method may further comprising folding the article along the fold lines, and optionally, placing the folded article in a package. The article may placed in a individual pack, for example a single wrap and further in an outer/distribution box, also called multi pack. Alternatively, it can packed directly in an outer/distribution box, also called multi pack.

Folding the article may comprise: folding the first side region on top of the central region along the first fold line, folding the second side region on top of the central region and the first region along the second fold line such that the first side region at least partially forms a first overlap region with the second side region; and, optionally, folding the lower end region over along the third fold line to overlap at least one of the first and second side regions and form at least partially a second overlap region. The step of folding the lower end region along the third fold line can be carried out: before folding the first and second side regions along their respective first and second fold lines; after folding the first and second side regions along their respective first and second fold lines; or after folding the first side region along the first fold line and before folding the second side region along the second fold line. This way the side regions and/or the lower end region may be folded on top of the topsheet, so that the body facing side of the absorbent article, which during use receives body exudate, is covered.

One of the challenges faced by users of male incontinence guards is unfamiliarity with the use of disposable hygiene articles and the manner in which they can be disposed of. It is therefore desirable to provide a disposable male incontinence guard in which the advantages associated with the present disclosure will be intuitive to the user. To guide the user to fold and dispose of articles according to the disclosure in a convenient and hygienic manner, a kit can be provided which comprises a male incontinence guard as described above, and a set of instructions or illustrations guiding the user to fold the article after use, and prior to disposal. Such instructions may be printed on the article (e.g. on garment facing surface thereof), on a package in which the article is provided, or a removable protector, e.g. a protector covering the fastening material of the article.

Further, the incontinence guard may be pre-folded along at least the first and the second fold lines.

Further objectives, features, and advantages of the disposable hygiene article according to the present disclosure will be apparent from the description below and the appended drawings. Objectives, features, and advantages of the method of manufacturing described herein will also be apparent.

BRIEF DESCRIPTION OF THE FIGURES

The present invention will now be described with reference to a number of non-limiting illustrative embodiments shown in the attached drawings, in which:

FIG. 2 shows schematically the cross-sectional view along line A-A in FIG. 1.

FIG. 3 shows schematically a plan view of the male incontinence guard of FIG. 1 in a first folded configuration.

FIG. 4 shows schematically a plan view of the male incontinence guard of FIG. 1, comprising a third fold line.

FIG. 6 shows schematically a plan view of a male incontinence guard according to another embodiment of the disclosure.

FIG. 7 shows schematically the male incontinence guard according to yet another embodiment of the disclosure.

FIG. 8 shows schematically a cross-sectional view along line A-A in according to a second embodiment of the disclosure.

FIGS. 9A-9C show schematically the steps for folding an incontinence guard according to the disclosure after use.

DETAILED DESCRIPTION OF ILLUSTRATIVE EMBODIMENTS

Figure 1:
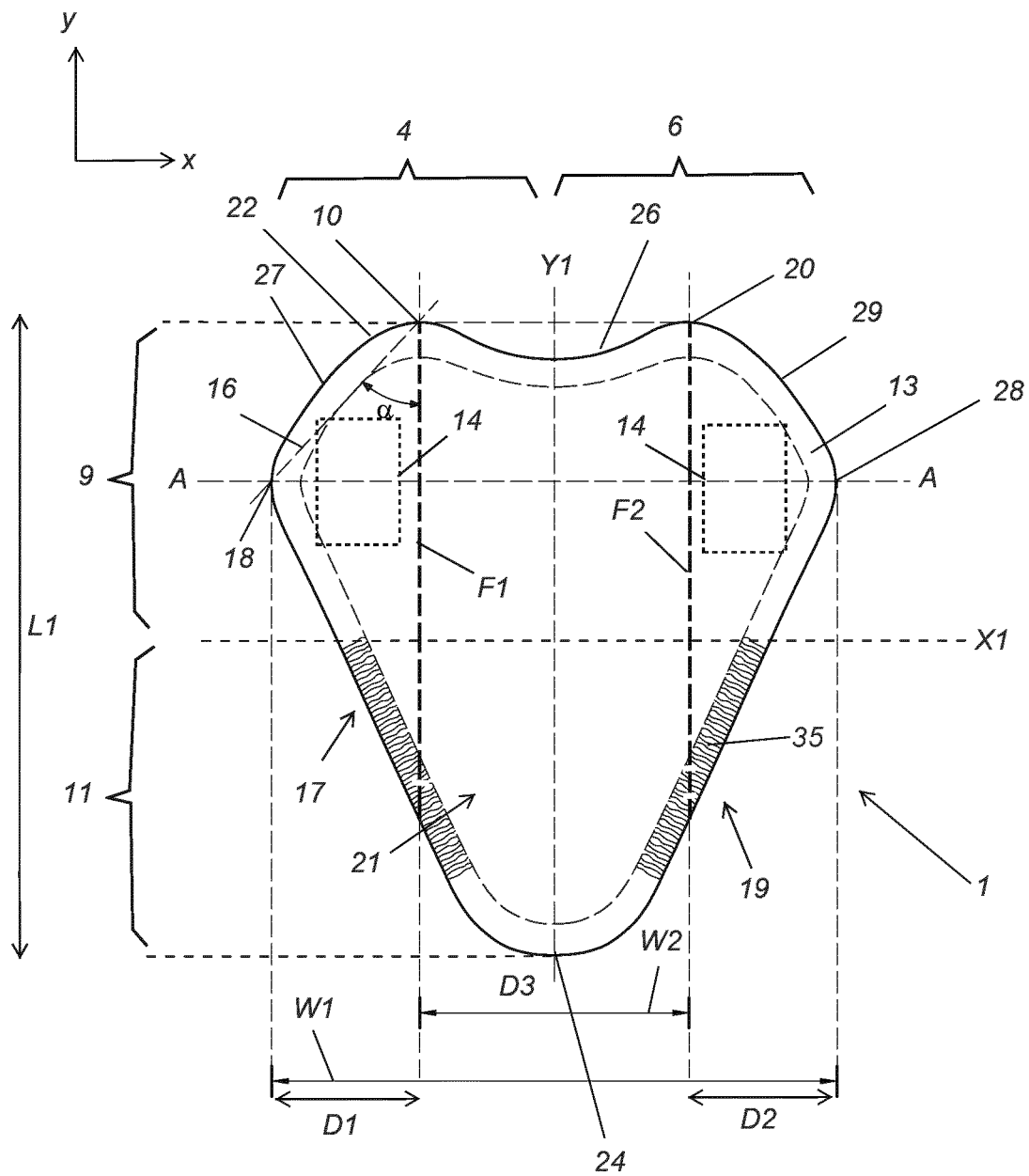
FIG. 1 shows schematically a plan view of a male incontinence guard according to the disclosure.

The present disclosure will be described with respect to particular embodiments and with reference to certain drawings but the disclosure is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the disclosure.

Furthermore, the terms first, second, third and the like in the description and in the claims, are used for distinguishing between similar elements and not necessarily for describing a sequential or chronological order. The terms are interchangeable under appropriate circumstances and the embodiments of the disclosure can operate in other sequences than described or illustrated herein.

Furthermore, the various embodiments, although referred to as "preferred" are to be construed as exemplary manners in which the disclosure may be implemented rather than as limiting the scope of the disclosure.

The term "comprising", used in the claims, should not be interpreted as being restricted to the elements or steps listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising A and B" should not be limited to devices consisting only of components A and B, rather with respect to the present disclosure, the only enumerated components of the device are A and B, and further the claim should be interpreted as including equivalents of those components.

The term "symmetrical" is intended to cover perfectly symmetrical articles and substantially symmetrical articles that may comprise minor deviations from a perfectly symmetrical form.

Different aspects of the present disclosure will be described more fully hereinafter with reference to the enclosed drawings. The embodiments disclosed herein can, however, be realized in many different forms and should not be construed as being limited to the aspects set forth herein.

FIG. 1 shows a plan view of a male incontinence guard 1 from above. The male incontinence guard 1 is an incontinence protector article which is designed and optimised to absorb light urine leakage for male users. For this reason, and as will be described in detail below, the incontinence guards are based on an absorbent structure for rapidly wicking away urine from the wearer in order to provide a dry, comfortable and odor-free feeling for the wearer. The embodiments described herein refer generally to disposable male incontinence guards, which means guards are specially adapted for the male anatomy and are not intended to be laundered or otherwise restored after use.

As shown in FIG. 1, the incontinence guard 1 has a longitudinal extension along a longitudinal axis Y1 and a transverse extension along a transverse axis X1. The longitudinal axis Y1 divides the guard 1 into a first portion 4 (the left hand portion as shown in FIG. 1) and a second portion 6 (the right hand portion as shown in FIG. 1). The longitudinal axis Y1 preferably divides the guard 1 into two halves of equal width, measured in the transverse direction x. The total width of the guard is $W_1$.

The transverse axis X1 divides the guard 1 into an upper portion 9 and a lower portion 11. The transverse axis X1 divides the upper portion 9 and the lower portion 11 and they are preferably of equal length, as measured in the longitudinal direction. The total length of the guard 1 is L1.

The upper portion 9 has a greater maximum extension measured in a transverse direction x (parallel to the transverse axis X1) than the maximum transverse extension of the lower portion 11. This means that the guard has its maximum width in the upper portion, providing a substantially inverted triangular shape, as shown in FIG. 1. In use, the upper portion 9 is intended to be oriented upwards towards the wearer's belly during use of the incontinence guard 1, whereas the lower portion 11 is intended to be facing downwards to cover the genital organs of the wearer during use. This means that, for instance, the corners and sides of the incontinence guard 1 may be more or less rounded, as shown in FIG. 1.

The incontinence guard 1 according to the embodiment shown in FIG. 1 is symmetrical with reference to the longitudinal axis Y1. Also, the guard 1 has a tapering shape, tapered from the widest point as measured in the transverse direction, to a point in the lower portion. Below the widest point, the guard 1 is provided with generally straight sides. In an alternative embodiment, the sides of the lower portion 11 may be convex, i.e. generally without being curved inwards. In other words, the sides of the lower portion 11 may be curved slightly outwardly, with respect to the longitudinal axis Y1.

As shown in FIG. 1, the guard 1 comprises a first fold line F1 and a second fold line F2. The first and second fold lines separate the guard into a first side region 17, a second side region 19, and a central region 21 between the first and second side regions. In the embodiment shown in FIG. 1, the first and second fold lines are arranged symmetrically with respect to each other about the longitudinal axis. However, as will be understood from the following description, symmetry between the first and second fold lines is not essential to obtain the advantages associated with the present disclosure.

The first and second fold lines F1, F2 are predetermined fold lines. That is, the first and second fold lines are lines along which folding of the article is facilitated, such that the article preferentially folds along the fold lines. The fold lines F1, F2 can be provided by pre-folding the article, or by a structural feature configured to provide a region of increased pliability along which the article can fold.

Fastening material 14 is disposed in the first and second side regions 17, 19. The fastening material 14 is provided on a garment facing surface of the backsheet. The backsheet can comprise a single layer, or multiple layers, e.g. a multi-layer laminate. Where the backsheet 3 comprises multiple layers, the garment facing surface of the backsheet 3 comprises the fastening material 14.

Providing fastening material in the first and second side regions 17, 19 provides multiple advantages. For example, fastening material in the outer edge regions of the article, at or near the widest point can secure the outer corners of the article to the user's undergarments, thereby minimizing the risk that the corners of the article become folded over during use. The positioning of the fastening material outside the first and second fold lines F1, F2 can ensure that the fastening material fastens the first and second side regions 17, 19 together when folded over the central region 21, along the fold lines F1, F2.

The first and second fold lines can be formed in the absorbent core 7. The first and second fold lines F1, F2 shown in FIG. 1 may comprise compression lines, embossing lines in the absorbent core 7, or channels of lower basis weight compared to surrounding regions of the core 7. Alternatively, the first and second fold lines F1, F2, can be provided by an edge of an additional layer such as an edge of the fastening material (e.g. when the fastening material 14 is a hook material) or an edge of and additional core layer.

The fastening material can also be provided as integrated hooks formed directly from the backsheet in a predetermined region. In such examples the edge of the hook region can provide the fold lines. A method of forming integrated hooks from the backsheet that can provide fold lines according to the disclosure is described in WO 2010/085492, the disclosure of which is herein incorporated by reference.

As shown in FIG. 1, the guard has a generally triangular shape and may optionally comprise rounded or truncated corners to better fit within the undergarments of the user.

The guard 1 is configured such that the first side portion 4 comprises a first (left) upper corner region and the second side portion 6 comprises a second (right) upper corner region. The first upper corner region comprises a first upper corner 10 and a first lower corner 18. The second upper corner region comprises a second upper corner 20 and a second lower corner 28. The upper and lower corners provide a rounded shape in the upper portion of the guard 1. Each of the first and second side regions 17, 19 may further comprise additional corner points. By providing upper and lower corner points, the shape in the upper portion 9 of the guard can be tailored to fit within the standard undergarments.

In the embodiment shown in FIG. 1, the lower corner points 18, 28 define the outermost points of the incontinence guard 1. The distance between the lower corner points 18, 28, i.e. the maximum width of the incontinence guard 1, may be defined by a first width $W_1$, and the distance between the upper corner points 10, 20 may be defined by a second width $W_2$, as indicated in FIG. 1. In the embodiment shown in FIG. 1, $W_2$ corresponds to the central region 21. However, the skilled person will appreciate that the upper corner points 10, 20 may be configured such that the width $W_2$ is larger or smaller than the central region 21.

The ratio between the value of the first width $W_1$ and the value of the second width $W_2$ is in the range of 30-80%, preferably in the range of 40-75%. Regarding the measurements of the first width $W_1$ and the second width $W_2$, it can be noted that the first width $W_1$ is in the range of 110-280 mm. Also, the second width $W_2$ is in the range of 50-151 mm.

The first lower corner point 18 and the first upper corner point 10 may be connected by a first outer side edge 27 which according to the embodiment may have an outwardly and slightly rounded shape. An imaginary straight line 16, which extends through the first lower corner point 18 and the first upper corner point 10, may also be defined. In a similar manner, the second lower corner point 28 and the second upper corner point 20 may be connected by a second outer side edge 29 which may have an outwardly and slightly rounded shape. The first and second outer side edges 27, 29 may extend outwards as regarded along the direction of the transverse axis X1, i.e. from the upper corner points 10, 20 to the lower corner points 18, 28.

The guard is bounded by an upper edge 22. The upper edge defines the upper most extent of the guard. Between the upper edge 22 of the guard 1 and the transverse axis X1, the guard comprises its widest point, which has a width $W_1$. Below the point of maximum transverse width, the guard tapers to a point 24. In the upper edge 22, an inwardly recessed curvature portion 26 may be provided. With reference to the embodiment shown in FIG. 1, it can be noted that the inwardly recessed curvature portion 26 has a radius in the range of 60-1400 mm, preferably in the range of 120-500 mm.

An angle α may be defined between the imaginary straight line 16 and the longitudinal axis Y1 or an axis parallel to said longitudinal axis Y1. The angle α may be defined between the intersection of the imaginary straight line 16 with an axis parallel to the longitudinal axis Y1 outside the upper portion 9 as shown in FIG. 1. The angle α may be defined between the intersection of the imaginary straight line 16 with the longitudinal axis Y1 outside the lower portion 11 (not shown). The angle α may be in the range of 12-78°, preferably in the range of 22-68°. A similar angle, according to the embodiments, may be defined between an additional imaginary straight line (not shown), which extends through the second lower corner point 28 and the second upper corner point 20, and the longitudinal axis Y1 or an axis parallel to said longitudinal axis Y1.

Furthermore, the incontinence guard 1 may comprise elasticized elements 35 which are arranged along the edge region 13 of the lower portion 11. The elasticized elements 35 may be in the form of elastic threads, an elastic foam, or an elastic laminate attached to the incontinence guard 1. The elasticized elements 35 may be in the form of an elasticized film which is attached to the incontinence guard 1, although other elastication means will be apparent to the skilled person.

As shown in FIG. 1, at least one of the first 17 and second 19 side regions comprises a fastening material 14 on the garment facing surface of the guard 1. In the preferred embodiment shown in FIG. 1, both the first and second side regions comprise fastening material 14. The fastening material can advantageously be arranged on the backsheet such that the fastening material 14 on the guard 1 is arranged symmetrically about the longitudinal axis y.

The fastening material is positioned in the first and second side regions 17, 19 such that when the first and second side regions are folded over, along the respective first and second fold lines F1, F2, the fastening material acts to secure the first and second side regions 17, 19 to each other, to hold the guard in a folded configuration (see FIG. 3). The fastening material 14 may comprise any materials suitable for their particular purposes, as will be discussed in further detail below.

FIG. 3 shows the incontinence guard 1 of FIG. 1 in a first folded configuration, where the first and second side regions 17, 19 overlap each other and forms a first overlap area 31. The first overlap area 31 may extend at least 10 mm in the transverse direction, more preferably at least 20 mm in the transverse direction, and more preferably at least 25 mm in the transverse direction. That is, the overlap area 31 has a length $D_4$ that extends in the transverse direction x.

The fastening material 14 in the first overlap area 31 may have an area comprising at least 30% of the first overlap area 31, more preferably at least 50% of the first overlap area 31, and more preferably at least 70% of the first overlap area 31.

In the first folded configuration, the first and second side regions 17, 19 may substantially completely cover an absorbing surface of the guard 1 in the upper portion 9 of the guard. That is, the body facing side of the absorbent article, which refers to the side facing the wearer during use that acts to receive body exudate in the upper portion of the guard, is covered. The first and second side regions 17, 19 may substantially completely cover the upper portion 9 of the guard.

Both the first side region 17 and the second side region 19 may comprise a fastening material 14 on the garment facing surface (see FIG. 1). The fastening material 14 may extend along an axis parallel to the transverse axis X1, and preferably across the widest portion of the guard. The fastening material 14 may have a greater maximum extension in the longitudinal direction y than the maximum extension of the fastening material 14 in the transverse direction.

The fastening material 14 in the first and second side regions 17, 19 may be arranged such that they are symmetrical and parallel to each other. Furthermore, the fastening material 14 may be formed in an area equal to the area of the side region 17, 19, preferably having an area equal to the area of part of the absorbent body 7 in the relevant side region 17, 19 (see FIG. 2).

To ensure that the first overlap area 31 is formed, particular distances may be defined. Thus, a first distance $D_1$ may be defined between an outermost edge of the first side region 17 and the first fold line F1, a second distance $D_2$ may be defined between an outermost edge of the second region 19 and the second fold line F2 and a third distance $D_3$ may be defined between the first and second fold lines F1, F2, and wherein $D_1+D_2>D_3$.

In FIG. 1 the first and second fold lines F1, F2 are parallel to each other, and extend in the longitudinal direction y. The distances $D_1$, $D_2$, and $D_3$ are thus measured in the transverse direction x, perpendicular to the longitudinal fold lines F1, F2.

The distances $D_1$, $D_2$, and $D_3$ together form a straight line, extending in the transverse direction x. As shown, $D_1+D_2+D_3$ can be equal to $W_1$, which is the maximum extension of the upper portion. Since $D_1+D_2>D_3$, when the first and second side regions are folded along fold lines F1, F2, they overlap with each other to form a region of overlap. It will be appreciated that the distances $D_1$, $D_2$, and $D_3$ can be chosen to ensure that a region of overlap is formed in examples in which the fold lines extend in a direction that is non-parallel to the longitudinal axis. Further, if the thickness of the product is severe the first distance D1 and the second distance D2 may be adjusted so that the side regions overlap.

In an example shown in FIG. 1, the distances may be defined wherein $D_1+D_2+D_3=W_1$ and wherein $D_3<\frac{1}{2}*W_1$. In another example, the outer edge of the first region 17 may be the first upper corner point 10 and the outer edge of the second region 19 may be the second upper corner point 20, and the distances may be defined wherein $D_1+D_2+D_3=W_2$ and wherein $D_3<\frac{1}{2}*W_2$. The outer edge of the first side region 17 may be a further corner point of the first side region 17, and the outer edge of the second side region 19 may be a further corner point of the second side region 19.

The value of the first width $W_1$ may be in the range of 110-280 mm which may be dependent on the size of the guard (XS, S, M, L, XL, etc.). One example is a guard 1 with first width $W_1$=190 mm, and distances $D_1$=60 mm, $D_2$=60 mm and $D_3$=70 mm resulting in a first overlap of 50 mm in the transverse direction x. Another example is a guard 1 with first width $W_1$=120 mm, and distances $D_1$=35 mm, $D_2$=35 mm and $D_3$=50 mm, resulting in a first overlap of 20 mm in the transverse direction. However, the thickness of the guard may influence the length D4 (see FIG. 3) of the first overlap. In the first example, where the calculated overlap is 50 mm, the overlap may be less than 50 mm if the product is thick. The overlap may for example be only 30 mm.

FIG. 2 shows a cross-sectional view along line A-A from FIG. 1. However, the guard shown in FIG. 2 comprises additional fastening material 14', which may optionally be present in any of the embodiments described herein.

The additional fastening material 14' is positioned in the central region 21 of the guard 1, and is covered by a release paper 12. Release paper 12 can be provided to protect adhesive fastening materials, however, the release paper 12 is an optional feature. Release paper may also be provided on the fastening material 14 in the first and second side regions 17, 19, if desired.

As shown in FIG. 2, the guard 1 comprises a fluid-impermeable backsheet 3 and a fluid-permeable topsheet 5. The incontinence guard 1 also comprises an absorbent body or core 7 which is disposed between the backsheet 3 and the topsheet 5. The backsheet 3, topsheet 5 and absorbent core 7 are shown in cross-section in FIG. 2. An alternative embodiment is shown in FIG. 8, and will be described in more detail later.

In use, the article is configured to be oriented with the backsheet 3 facing towards the undergarment(s) of the user and the topsheet 5 facing toward the body of the user. The backsheet 3 and the topsheet 5 extend laterally outside of the absorbent body 7 along the whole perimeter of the incontinence guard 1, and are joined to each other around the perimeter of the core 7 to contain the absorbent core 7 between the topsheet 5 and the backsheet 3. The backsheet 3, topsheet 5 and the absorbent body 7 may comprise any materials suitable for their particular purposes, as will be discussed in further detail below.

The backsheet 3 provides the garment facing surface of the article (i.e. the surface closest to the user's undergarments in use). The backsheet 3 can comprise a single layer or a multiple layers, e.g. a multi-layer laminate. In examples comprising a backsheet with multiple layers, the fastening material 14 is provided on the garment facing surface of the guard 1. The garment facing surface can thus comprise a fluid-impermeable layer, a soft-touch outer layer (such as a non-woven material) or another layer forming the outer layer of the backsheet. An acquisition layer (not shown) may also be provided between the absorbent body 7 and the topsheet 5. The acquisition layer may be adapted to quickly receive and temporarily store discharged liquid before it is absorbed by the absorbent core/body.

Fastening material 14 is shown in the outer side regions 17, 19 of the guard 1. In the embodiment shown in FIG. 2, the backsheet 3 provides the garment facing surface of the article and the fastening material 14 is provided on the backsheet.

In some embodiments, additional fastening material 14' may be provided in the central region 21 of the article (Not shown in FIG. 1). Additional fastening material 14' is shown in FIG. 2. The fastening material 14 and/or the additional fastening material 14' may be covered by a protective cover 12, such as a release paper. Release paper 12 is particularly advantageous when the fastening material 14 or the additional fastening material 14' is an adhesive. Additional fastening material will be discussed in more detail with reference to FIGS. 3 to 8. Each fastening material 14, 14' may have a separate release paper or one larger release paper may cover two or more fastening materials.

As shown in FIGS. 1 and 2, the backsheet 3 and the topsheet 5 may be connected to each other along an edge region 13, which extends around the perimeter of the incontinence guard 1. The absorbent body 7 may be of a size having an area which is slightly smaller than the area of the backsheet 3 and the topsheet 5. The edge region 13 may have substantially the same width along the entire perimeter of the incontinence guard 1. In other words, the absorbent body 7 may be arranged to follow the perimeter of the incontinence guard 1 so that the distance between the outer edge of the absorbent body 7 and the outer edge of the guard 1 remains generally equal along the edge region 13.

According to an embodiment, the backsheet 3 is constituted by a fluid-impermeable and breathable layer such as a polymeric film, for example a film of polyethylene or polypropylene. According to different embodiments, the materials which can be used for manufacturing the backsheet 3 include thin and flexible fluid impermeable plastic films, or fluid impermeable nonwoven materials, fluid impermeable foams and fluid impermeable laminates.

According to the embodiment shown in the drawings, the backsheet 3 is formed by a single layer, but can alternatively be formed by a multi-layered structure, i.e. a laminate, wherein at least one layer is fluid impermeable. Furthermore, the backsheet 3 can optionally be elastic in any direction. Also, backsheet materials that are not fully fluid impermeable but only resistant to fluid penetration may be used, particularly in cases where relatively small amounts of urine are expected to be absorbed by the incontinence guard 1. According to further embodiments, the backsheet 3 may be breathable, implying that air and vapor may pass through the backsheet 3. Furthermore, the backsheet 3 may optionally have an outer, garment-facing surface of a textile material such as nonwoven.

Furthermore, the topsheet 5 is according to an embodiment formed by a fluid permeable nonwoven fabric or film. The topsheet 3 is sufficiently fluid permeable to allow discharged body fluids such as urine to penetrate through the thickness of the topsheet 5. Also, the topsheet 5 is suitably manufactured from a material which is compliant and soft-feeling to the skin of the wearer.

According to different embodiments, the topsheet 5 may be manufactured from various web materials such as woven and nonwoven webs and films, foams, or combinations of the above-mentioned materials. The nonwoven materials to be used for the topsheet 5 may be for example carded resin bonded materials, carded through-air bonded materials, spunbond-meltbond-spunbond materials, carded hydroentangled materials or carded thermobonded materials. The topsheet 5 may also have elastic properties which allow it to be stretchable. According to an additional embodiment, the topsheet 5 may be in the form of a perforated plastic film which then serves as a liquid-permeable sheet.

Folding of the guard 1 along the first and second fold lines F1, F2 will now be described in more detail with reference to FIG. 3.

FIG. 3 shows the guard of FIG. 1 folded along first and second fold lines F1, F2 to form a first folded configuration. As shown in FIG. 3, with the guard 1 in the first folded configuration, a first overlap region 31 is formed, in which the first and second side regions 17, 19 overlap or overlie each other on top of the topsheet 5, so that the body facing side of the absorbent article, which during use receive body exudate, is covered. The fastening material 14 (not shown in FIG. 3) extends at least partially within the first overlap region 31 to ensure that the first and second side regions 17, 19 are secured together when in the first folded configuration. It will be appreciated that the first and second side regions 17, 19 can be secured together with fastening material provided on only one of the first and second side regions 17, 19. However, such a configuration required the first and second side regions 17, 19 to be folded in a predetermined order in order for the guard to be secured in the first folded configuration. It is thus preferred that fastening material 14 is provided on both the first and second side regions 17, 19 such that it extends at least partially in the first overlap region 31.

A further advantage of embodiments in which the first and second side regions 17, 19 are provided with fastening material, is that the guard 1 as shown in FIG. 3 can be rolled or folded from the lower end in an upward direction towards the first overlap region 31. The lower portion of the guard can thus be secured in place over the first and second folded side regions 17, 19 to provide an enclosed parcel, in which substantially all of the absorbent surface of the guard 1 is enclosed within the parcel. Such a configuration allows for hygienic storage of the article until a suitable disposal facility can be found.

As shown in FIG. 4, the guard 1 described in connection with FIG. 1 may further comprise a third fold line F3 in the lower portion 11 to define a lower end region 23. The third fold line F3 may be provided in the upper portion 9 and/or lower portion 11 of the guard 1, preferably in the lower portion 11. The third fold line F3 may extend in the transverse direction parallel to the transverse axis X1 in the upper portion 9 or the lower portion 11 of the guard 1, preferably in the lower portion 11. The third fold line F3 may extend in a direction perpendicular to the longitudinal axis Y1. The third fold line F3 may extend in a direction intersecting at least one of the first fold line F1 and the second fold line F2. The third fold line F3 may extend in a direction perpendicular to at least one of the first fold line F1 and the second fold line F2.

In embodiments, at least one of the fold lines F1, F2, F3 may be discontinuous. This means that the fold line may be in the shape of a plurality of lines and/or dots with space in between said plurality of lines and/or dots, such that connecting the plurality of lines and/or dots would result in a full fold line. Furthermore, at least one of the fold lines F1, F2, F3 may be curved, which may be dependent on for example the shape of the guard 1 and/or the elasticized elements 35.

In embodiments, at least one of the fold lines F1, F2, F3 may be formed by grooves which may be created by compression of the absorbent body 7. This means that a compressed region of the absorbent body 7 or score lines may be formed in the absorbent body 7. Furthermore, at least one of the fold lines F1, F2, F3 may be formed by channels in the absorbent body 7 which may be created by removing absorbing material from the absorbent body 7 in a desired pattern. The channels may have a lower basis weight than the surrounding regions of the absorbent body 7. Furthermore, at least one of the fold lines F1, F2, F3 may be formed by perforations in the topsheet 5, and/or absorbent body 7 which may be created by puncturing holes in the topsheet 5 and/or absorbent body 7 in a desired pattern. Furthermore, at least one of the fold lines F1, F2, F3 may be formed by one of weld lines, embossed lines, and cut lines, preferably created by a laser system or ultrasonic system for welding, cutting, and embossing of the garment facing surface, the surface of the topsheet, and/or the absorbent body 7 in a desired pattern. Another method may be thermal welding, cutting and embossing. Other mechanical means of forming folding lines, such as pre-folding, will be discussed in further detail below.

The first fold line F1 may be formed extending in a first folding region (not shown). The first folding region may be formed in between the first side region 17 and the central region 21. The first folding region may be partially formed in at least one of the first side region 17 and the central region 21, preferably in the first side region 17. The second fold line F2 may be formed extending in a second folding region. The second folding region may be formed in between the second side region 19 and the central region 21.

The second folding region may be partially formed in at least one of the second side region 19 and the central region 21, preferably in the second side region 19. Furthermore, at least one of the first and second folding regions may be substantially free of fastening material 14, 14'. Furthermore, at least one of the first and second fold lines F1, F2 may extend in the relevant folding region that is substantially free of fastening material 14, 14'.

The third folding line F3 may be formed extending in a third folding region. The third folding region may be formed in between the lower end region 23 and the upper end region 25. The third folding region may be partially formed in the lower end region 23. The third folding region may be substantially free of fastening material 14, 14'. Furthermore, at least the one of the first, second and third fold lines F1, F2, F3 may extend in the relevant folding region that is substantially free of fastening material 14, 14'.

Figure 5:
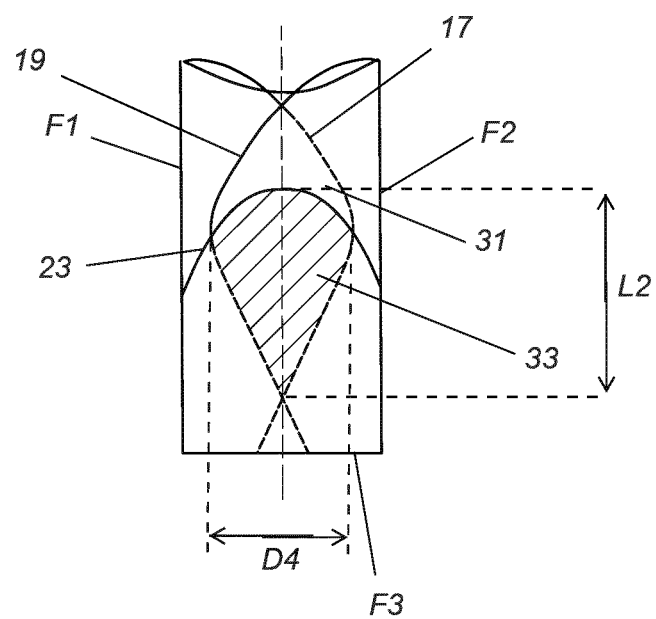
FIG. 5 shows schematically the male incontinence guard of FIG. 4 in a second folded configuration.

As shown in FIG. 5, with the guard in the first folded configuration (as shown in FIG. 3), the lower end region 23 may be configured to be folded along the third fold line F3 to form a second folded configuration in which the lower end region 23 at least partially overlaps at least one of the first side region 11 and the second side region 13 to form a second overlap area 33. The first overlap area 31 and the second overlap area 33 overlap each other when the guard is in a folded configuration, preferably in the second folded configuration. Furthermore, the fastening material 14 is at least partially disposed in the second overlap area 33.

The fastening material 14 (not shown in FIG. 5) may be configured to fasten the lower end region 23 to at least one of the first side region 17 and the second side region 19 in the second folded configuration.

In alternative embodiments, the lower end region 23 may be folded first along the third fold line F3 over the central region 21, and the first side region 17 may then be folded along the first fold line F1 and thereafter the second side region 19 may be folded along the second fold line F2. That is, both side regions 17, 19 being folded over the lower end region 23 to form the fully folded configuration, in which the first side region 17 at least partially overlaps the second side region 19 to form a first overlap area 31 and at least one of the first side region 17 and the second side region 19 at least partially overlaps the lower end region 23 to form the second overlap area 33.

Another example of the further folded configuration (not shown) may be the first side region 17 being folded along the first fold line F1 over the central region 21, the lower end region 23 being folded along the third fold line F3 over the central region 21 to at least partially overlap the first side region 17, and the second region 19 being folded along the second fold line F2 over central region 21 thereafter, to form the fully folded configuration.

The second overlap area 33 may have length L2 of at least 10 mm in the longitudinal direction, more preferably at least 15 mm in the longitudinal direction, and more preferably at least 20 mm in the longitudinal direction. The second overlap area 33 may have an area comprising at least 30% of the first overlap area 31, preferably at least 50% of the first overlap area 31, and more preferably at least 70% of the first overlap area 31.

The fastening material 14 in the second overlap area 33 may have an area comprising at least 30% of the second overlap area 33, preferably at least 50% of the second overlap area 33, and more preferably at least 70% of the second overlap area 33.

Furthermore, the fastening material 14 may be at least partially disposed in the second overlap area 33. The fastening material 14 may be configured to fasten the lower end region 23 to at least one of the first side region 17 and the second side region 19 in the further folded configuration.

Furthermore, with the guard in the second or further folded configuration, the first side region 17, the second side region 19 and the lower end region 23 may cooperate to substantially completely cover an absorbent surface of the guard 1. That is, the topsheet and any underlying material such as the absorbent body/core.

The incontinence guard 1 may be pre-folded along at least one of the first, second and third fold lines F1, F2, F3. The guard 1 may be pre-folded in the above mentioned first folded configuration, wherein the first and second side regions 17, 19 are pre-folded along the first and second fold lines F1, F2. The guard 1 may be pre-folded in the above mentioned second and further folded configurations, wherein the first and second side regions 17, 19 and the lower end region are pre-folded along the first, second and third fold lines F1, F2, F3. The pre-folding of the guard 1 may result in the first, second and third fold lines F1, F2, F3 being formed, and preferably used to fold and dispose of the guard 1 after use.

It will be appreciated that different fold lines configurations can be provided to provide a conveniently disposable parcel as shown in FIGS. 3 and 5.

As shown in FIG. 6, the guard 1 can comprise first and second fold lines F1, F2 that extend at an angle β with respect to the longitudinal axis Y1. In the embodiments shown in FIG. 1, the first and second fold lines F1, F2 extend parallel to the longitudinal axis Y1. Hence, in FIG. 1, β=0.

In the embodiment shown in FIG. 6, β≠0 and the first and second fold lines F1, F2 diverge away from each other as they extend in an upward direction (i.e. towards the top edge of the guard 1). The angle β is preferably less than 60 degrees, more preferably less than 45 degrees, and more preferably less than 30 degrees.

As shown in FIG. 6, the first side region 17, the second side region 19 and the central region 21 comprise the fastening material 14, on the garment facing surface. The fastening material 14, may be arranged to extend in the first and second side regions 17, 19 and the central region 21 in a discontinuous pattern (not shown) or a continuous patterns as shown in FIG. 7. The fastening material 14 extends across the first central region 21 and into the first and second side regions 17, 19 such that it extends in at least the first 31 and preferably the second 33 overlap region when the guard is in the folded configuration. The fastening material 14 extends in the upper portion 9 of the guard 1.

In the embodiment illustrated in FIG. 6, the fastening material 14 comprises an elongate strip or region of fastening material arranged to extend in the transverse direction x. As shown, the fastening material 14 may be arranged symmetric with reference to the longitudinal axis Y1.

Additional fastening material 14' may be provided in the central region 21 on the garment facing surface. The additional fastening material 14' may comprise an elongate strip or region arranged to extend along the longitudinal axis Y1, preferably along the longitudinal axis Y1 as shown in FIG. 6. In FIG. 6, the additional fastening material 14' is arranged in the central region 21. The additional fastening material 14' extends in the lower portion 11 and extends into the upper portion 9. However, in some examples additional fastening material 14' may be provided only in the lower portion 11 or only in the upper portion 9. The additional fastening material 14' may have a greater maximum extension along the longitudinal axis Y1 than the maximum extension of the additional fastening material 14' along the transverse axis X1. The additional fastening material 14' may be formed symmetric with reference to the longitudinal axis Y1.

The fastening material 14 and the additional fastening material 14' shown in FIG. 6 comprise continuous elongate strips or regions of fastening material. However, the skilled person will appreciate that the fastening material 14 of the additional fastening material 14' may be implemented as a patterned region of fastening material.

The fastening material 14 and the additional fastening material 14' may be arranged to extend in a manner which forms in combination a substantially T-shaped arrangement. Such a configuration allows the article to be secured within the user's undergarments in the central region and the side regions 17, 19. This allows secure placement of the guard 1, and prevents the corners of the guard 1 from folding over during use.

Further configurations are envisaged in which the fastening material and any additional fastening material are arranged with substantially 'U-', 'V-', 'X-', 'Y-', 'Z-' shaped configurations.

An angle γ may be defined between the first and second fold lines F1, F2, wherein the angle γ may be in the range of 0-90°. This means that when the angle γ is not equal to 0° the first and second fold lines F1, F2 are not parallel to each other. The fold lines F1, F2 may diverge from each other (and the longitudinal axis Y1) as they extend in an upward direction. That is, the distance measured in the transverse direction x between opposing points on the first and second fold lines F1, F2 increases as the fold lines F1, F2 extend from the lower end of the guard 1 towards the upper end of the guard 1. The fold lines may meet or intersect in the lower portion 11 of the guard 1, or they may be spaced apart from each other at the lower edge of the guard 1. Since the first and second fold lines F1, F2 are preferably (although not essentially) symmetrical with each other about the longitudinal axis Y1, γ is preferable 2β.

Although not shown in the illustrated embodiments, the first and second fold lines F1, F2 may be asymmetric to each other, as long as the side regions at least partly overlaps when the side regions are folded along the fold lines.

The fastening material 14 and the additional fastening material 14' in the illustrated embodiments may comprise a mechanical fastening material. The mechanical fastening may comprise a hook material, preferably a hook fastening material. The hook material may be integrally formed in the backsheet 3 or in the garment facing surface on the backsheet 3. Furthermore, the hook material may be a hook patch. A method for forming an integrated hook material is described in WO2010/085492, the contents of which is incorporated by reference. Mechanical fastening materials are applicable to all embodiments described.

Advantageously, when the fastening material 14 is a mechanical fastening material such as a hook patch, the topsheet 5 may comprise a material configured to engage a hook material. Suitable materials include a woven material, a non-woven material, a spunbound material, a carded material, a spunlace material, or a combination thereof.

The fastening materials 14 and the additional fastening material 14' can also comprise an adhesive fastening means. The adhesive material may be coated on the garment facing surface of the backsheet 3. Where the fastening material 14 comprises an adhesive, the material comprised in the topsheet 5 may be further configured to engage the adhesive material. Suitable materials include polyolefinic aperture film, a laminate or a combination thereof with the above mentioned materials comprised in the topsheet 5.

It will be appreciated that the fastening material 14 can comprise a first type of fastening material, whilst the additional fastening material comprises a second type of fastening material. For example, the additional fastening material 14' can be an adhesive fastening, whilst the fastening material 14 in the first and second side regions 17, 19 can be a mechanical fastener. Alternatively, the fastening material 14 in one side region may be adhesive and the other fastening material 15 in the other side region may be a mechanical fastening FIG. 7 shows another embodiment of the disclosure, comprising first and second fold lines F1, F2 for creating the first overlap region 31, and further comprising additional fold lines F3, F4, which can further aid folding of the guard, and improve the fit of the guard 1 against the user's body. As shown in FIG. 7, the guard 1 is of substantially similar shape to the guard 1 discussed above with reference to FIG. 6. It comprises a wider transverse extension in the upper portion and a narrower transverse extension in the lower extension to provide a substantially triangular shape.

The first and second fold lines F1, F2 are angled with respect to the longitudinal axis Y1, similar to the fold lines F1, F2 of FIG. 6. The angle defined between the fold line F1 and the longitudinal axis Y1 is shown as angle β. Since the first and second fold lines F1. F2 are symmetrical in the illustrated embodiments, the angle between the second fold line F2 and the longitudinal axis Y1 is also β.

In the embodiment shown in FIG. 7, the guard 1 comprises additional fold lines F3 and F4 laterally outwards of the first and second side fold lines F1, F2, in the first and second side regions 17, 19. They may be arranged parallel with the first and the second fold lines F1, F2 or at an angle.

In the embodiment shown in FIG. 7, the first and second fold lines F1, F2 and the additional fold lines F3, F4 are formed by edges or discontinuities (e.g. gaps) in the fastening material 14, 14'. The guard in FIGS. 6 and 7 can comprise the third folding line F3 in FIG. 4 (not shown in FIGS. 6 and 7) so that the lower end region may be configured to be folded along the third fold line to form the second folded configuration.

As shown in FIG. 7, fastening material 14, 14' is provided in strips across the garment facing surface of the guard. Between each of the strips of fastening material, a space extends in which no fastening material is provided. Because the fastening material 14, 14' comprises an additional layer (i.e. a hook patch) adhered to the garment facing surface, or a region of the garment facing surface that is relatively less pliable than the remainder of the article (e.g. due to ultrasonic treatment of the garment facing surface to create a region of hook material), bending is facilitated along the fold lines formed by the gaps between the regions of fastening material.

FIG. 8 shows a cross-sectional view of another embodiment of the disclosure of an absorbent article having the same outer contour as described in relation to FIG. 1 at the cross section taken along line A-A in FIG. 1. As shown in FIG. 8, the difference between the cross section in FIG. 2 is that the core 7, i.e. absorbent body 7 comprises a first layer 7a and a second layer 7b between the topsheet 5 and the backsheet 3. The second layer extends in the central portion 21 of the guard 1. The core 7 therefore has increased thickness in the central region 21 of the core compared to the first and second side regions 17, 19 of the guard 1. As shown in FIG. 8, the outer edge of the second layer 7b provides the first and second fold lines F1, F2. The fastening material 14 is thus provided transversally outward of the second layer 7b, in the region of the core 7 comprising only the first layer 7a. As in previous embodiments, the fastening material is positioned such that it extends at least partially across the first overlap region 31, and preferably the second overlap region 33.

Additional fastening materials 14' are arranged in the central region 21 of the guard 1, with release paper 12 providing a removal protective covering on top of it.

In the embodiment shown in FIG. 8, the first layer 7a is positioned adjacent to the fluid permeable topsheet 5, whilst the second layer 7b is positioned adjacent to the backsheet 3. This configuration provides a relatively smooth, flat surface towards the user's body. However, the positioning of the first and second layers 7a, 7b of the core 7 can be reversed.

A process for folding a male incontinence guard according to the disclosure and described in connection with FIG. 1 will now be described with reference to FIG. 9-C. Advantageously, the fold lines F1, F2 (and optional additional fold lines) facilitate folding of the guard 1 before use (e.g. prior to packaging) and after use, ready for disposal.

As shown in FIG. 9A, the first side region 17 of the guard 1 is folded along the first fold line F1, over the central region 21. The guard 1 is folded such that the first side region 17 is folded over the absorbent surface of the guard, i.e. over the topsheet 5 and any underlying material, such as the absorbent core, i.e. body.

As shown in FIG. 9B, in a second step, the second side region 19 is folded over the central region 21 along the second fold line F2. Once folded over, the body facing surface (i.e. the topsheet 5) of the second side region 19 contacts the fastening material 14 on the first side region 17, in the first overlap region 31 and hence attaches the two side regions 17, 19 to each other (as shown in FIG. 3).

As shown in FIG. 9C, in a final step the lower end region 23 is folded over such that its body facing surface (i.e. the topsheet) is secured to the fastening material 14 on the first and second side regions 17, 19 to form a securely closed parcel in which all or almost all of the absorbent surface of the guard in contained within the parcel (as shown in FIG. 5). Should the user remove and replace the article in a washroom without appropriate disposal facilities, the guard can be stored in the folded configuration until suitable disposable facilities can be accessed.

It will be understood that the article may be packaged in the folded configuration shown in FIG. 9C. For packaged articles, the folding steps may take place with protective coverings sealed against the fastening material (especially in embodiments comprising adhesive fasteners). Before use, the user can unfold the article, remove the protective covers (where present), and secure the guard in place.

After use, the user refolds the article into the folded configuration in which the article was packaged, thereby enclosing the absorbent surface of the guard ready for convenient disposal. Pre-folded articles may therefore inform the user of a convenient method of folding the article prior to disposal.

To inform the user regarding proper disposal of the article, instructions in the form of written instructions or illustrations may be provided with a packaged article, where the guard can be pre-folded or not pre-folded. The instructions may be provided on a packaging material, on a protective release paper, or on a surface of the guard. Providing disposal instructions on a surface of the guard may be advantageous because such instructions will be visible when the article is removed from the undergarment of the user. A kit can thus be provided comprising a male incontinence guard 1 as described above, a set of instructions for disposing of the article, and optionally, an outer package.

It will be understood that the invention is not limited to the embodiments described above but can be varied within the scope of the appended claims. For example, the particular shape of the incontinence guard 1 as shown in FIGS. 1 and 2 should not be considered as limiting the invention.

The materials chosen for the core, outer layers and fastening material(s) can also be varied. Fastening materials of various kinds are known in the art. Fastening materials suitable for use in connection with the present invention will be apparent to the skilled person. The skilled person will also understand in light of the present disclosure that the fastening can be configured to hold or secure the guard in the folded configuration when dry (i.e. before use) and after the absorbent core has absorbent a quantity of liquid, when it is generally bulkier and stiffer than an unused article.

The surface area of the fastening material and the fastening means (e.g. mechanical fastening, friction fastening, or adhesive fastening) can depend of the absorbency of the article and the structure of the fold lines. Higher absorbency guards may require stronger fastening to ensure the guard remains in the folded configuration because the absorbent core may become stiffer as the volume of liquid retained therein increases. Moreover, the nature and number of fold lines may increase or decrease the strength requirements of the fastening means due to the increase pliability of the guard provided by the fold lines.

Furthermore, the materials and dimensions used for the different layers forming the absorbent article 1 can be varied.

The invention claimed is:

1. A male incontinence guard comprising a fluid-impermeable backsheet, a fluid-permeable topsheet forming a body-facing surface of the guard, and an absorbent body arranged between said backsheet and said topsheet, said guard having a longitudinal extension along a longitudinal axis and a transverse extension along a transverse axis, said transverse axis dividing said guard into an upper portion and a lower portion, said upper portion having a greater maximum extension in a transverse direction parallel to transverse axis than the maximum extension of the lower portion in the transverse direction;

wherein the guard is divided into a first side region, a second side region, and a central region located between said first and second side regions in the transverse direction, wherein a first fold line is provided between the first side region and the central region and a second fold line is provided between the central region and the second side region, wherein the first side region is configured to be folded along the first fold line over the central region;

wherein the second side region is configured to be folded along the second fold line over the central region such that the first side region at least partially overlaps the second side region to form a first overlap region, wherein at least one of the first and second side regions, in the upper portion of the guard, comprises a fastening material on the backsheet of the incontinence guard, wherein the fastening material is a hook patch, a region of hooks integrally provided in the backsheet, or an adhesive, wherein the fastening material is at least partially disposed in the first overlap region, wherein a first distance D1 is defined between an outermost edge of the first side region and the first fold line; a second distance D2 is defined between an outermost edge of the second side region and the second fold line;

a third distance D3 is defined between the first and second fold lines, and D1 +D2 >D3, where D1, D2, and D3 are measured in the transverse direction and together form a straight line, and wherein the fastening material on the backsheet of the incontinence guard is configured to fasten the guard to an inside of an undergarment during use.

2. The incontinence guard according to claim 1, wherein the fastening material is further configured to fasten the first and second side regions to each other in a first folded configuration when the first and second side regions are folded along the first and second fold lines.

3. The incontinence guard according to claim 1, wherein the first overlap region is at least 10 mm in the transverse direction.

4. The incontinence guard according to claim 1, wherein the fastening material in the first overlap region has an area comprising at least 30% of the area of the first overlap region.

5. The incontinence guard according to claim 2, wherein, in the first folded configuration, the first and second side regions substantially completely cover an absorbing surface of the guard in the upper portion of the guard.

6. The incontinence guard according to claim 1, wherein the first side region and the second side region, in the upper portion of the guard, each comprise a fastening material on the backsheet.

7. The incontinence guard according to claim 1, wherein the first and second fold lines are parallel to each other.

8. The incontinence guard according to claim 1, wherein the first and second fold lines extend in a longitudinal direction (y), which is parallel to the longitudinal axis.

9. The incontinence guard according to claim 1, wherein the first and second fold lines are symmetric to each other with respect to an axis.

10. The incontinence guard according to claim 1, wherein the guard comprises a third fold line to define a lower end region below the third fold line.

11. The incontinence guard according to claim 10, wherein, with the guard in the first folded configuration, the lower end region is configured to be folded along the third fold line to form a second folded configuration in which the lower end region at least partially overlaps the first and second side regions to form a second overlap region.

12. The incontinence guard according to claim 11, wherein, when the guard is in the second folded configuration, the first and second side regions, and the lower end region cooperate to substantially completely cover an absorbent surface of the guard.

13. The incontinence guard according to claim 11, wherein the first overlap region and the second overlap region at least partially overlap each other when the guard is in the second folded configuration.

14. The incontinence guard according to claim 10, wherein the third fold line extends in the transverse direction.

15. The incontinence guard according to claim 10, wherein the third fold line is perpendicular to at least one of the first and second fold lines.

16. The incontinence guard according to claim 10, wherein the third fold-line intersects the first fold line and/or the second fold line.

17. The incontinence guard according to claim 1, wherein:
at least one of the fold lines is discontinuous,
at least one of the fold lines is curved, or
at least one of the fold lines comprises an embossed line.

18. The incontinence guard according to claim 1, wherein the guard is pre-folded along at least one of the fold lines.

19. The incontinence guard according to claim 1, wherein the guard comprises an additional layer in the central region of the guard, and wherein at least one of the fold lines is formed by an edge of the additional layer.

20. The incontinence guard according to claim 19, wherein the additional layer comprises an additional absorbent layer, a film, or a reinforcing layer.

21. The incontinence guard according to claim 1, wherein:
at least one of the fold lines is formed by an edge of the fastening material,
at least one of the fold lines is formed by a compressed region of the absorbent body or a score line formed in the absorbent body,
at least one of the fold lines is formed by a channel having a lower basis weight than the surrounding regions of the absorbent body, or
at least one of the fold lines is formed as a weld line.

22. The incontinence guard according to claim 1, wherein the mechanical fastening material is integrally formed in the backsheet.

23. The incontinence guard according to claim 1, wherein the topsheet comprises a material configured to engage a hook fastening.

24. The incontinence guard according to claim 1, wherein the fluid-impermeable backsheet forms a garment-facing surface of the guard, wherein the central region comprises an additional fastening material on the garment facing surface.

25. The incontinence guard according to claim 1, wherein at least the first and second fold lines extend in a folding region that is substantially free of fastening material.

26. A method for manufacturing a male incontinence guard, having a longitudinal extension along a longitudinal axis and a transverse extension along a transverse axis, said transverse axis dividing said guard into an upper portion and a lower portion, said upper portion having a greater maximum extension in a transverse direction, which extends in a direction parallel to the transverse axis, than the maximum extension of the lower portion in the transverse direction, said method comprising:
providing a fluid-impermeable backsheet;
providing a fluid-permeable topsheet;
providing an absorbent body arranged between said backsheet and said topsheet;
wherein said first and second fold lines divide the guard into a first side region, a second side region and a central region, wherein the first fold line is defined between the first side region and the central region and the second fold line is defined between the central region and the second side region, and wherein the first side region is configured to be folded along the first fold line over the central region,
wherein the second side region is configured to be folded along the second fold line over the central region such that the first side region at least partially overlaps the second side region to form a first overlap region,
wherein a first distance D1 is defined between an outermost edge of the first side region and the first fold line; a second distance D2 is defined between an outermost edge of the second side region and the second fold line; a third distance D3 is defined between the first and second fold lines, and D1 +D2 >D3, where D1, D2, and D3 are measured in the transverse direction and together form a straight line, and
providing a fastening material on a garment-facing side of incontinence guard in at least one of the first and second regions, wherein the fastening material is disposed at least partially in the first overlap region, wherein the fastening material on the garment-facing side of the guard is provided on the upper portion of the guard, wherein the fastening material is a hook patch, a region of hooks integrally provided in the backsheet, or an adhesive, and wherein the fastening material on the garment-facing side of the guard is configured to fasten the guard to an inside of an undergarment during use.

27. The method according to claim 26, further comprising the step of forming a third fold line to define a lower end region below the third fold line.

28. The method according to claim 26, wherein at least one of the fold lines is formed by embossing.

29. The method according to claim 26, wherein the guard comprises an additional layer in the central region of the guard, and wherein at least one of the fold lines is formed by an edge of the additional layer.

30. The method according to claim 29, wherein the additional layer comprises an additional absorbent layer, a film, or a reinforcing layer.

31. The method according to claim 26, wherein at least one of the fold lines is formed by an edge of the fastening material.

32. The method according to claim 26, wherein the method further comprises:
    folding the first side region on top of the central region along the first fold line;
    folding the second side region on top of the central region and the first region along the second fold line such that the first side region at least partially forms a first overlap region with the second side region; and, optionally,
    folding the lower end region over along the third fold line to overlap at least one of the first and second side regions and form at least partially a second overlap region with at least one of the first and second side regions.

33. The method according to claim 32, wherein the step of folding the lower end region along the third fold line is carried out:
    before folding the first and second side regions along their respective first and second fold lines;
    after folding the first and second side regions along their respective first and second fold lines; or
    after folding the first side region along the first fold line and before folding the second side region along the second fold line.

34. The method according to claim 32, wherein the method further comprises placing the folded guard in a package.

35. A kit comprising:
    a male incontinence guard according to claim 1; and
    a set of instructions directing a user to fold the guard along at least the first and second fold lines after use, prior to disposal.

36. The kit according to claim 35, wherein guard is pre-folded along at least the first and second fold lines.

37. The kit according to claim 35, wherein the guard is provided in a package.

38. The kit according to claim 35, wherein the guard further comprises a removable protector for covering at least one region of fastening material.

39. The kit according to claim 38, wherein the instructions are provided on the package, the backsheet, on an instruction folder and/or the removable protector.

40. The method according to claim 26, wherein the first side region and the second side region, in the upper portion of the guard, each comprise a fastening material on the backsheet.

* * * * *